(12) United States Patent  (10) Patent No.: US 8,449,900 B2
Volby  (45) Date of Patent: *May 28, 2013

(54) PESTICIDE STRIPS FOR CONTROL OF MITES IN HONEYBEES

(75) Inventor: Stuart Allen Volby, Hackensack, MN (US)

(73) Assignee: Mann Lake, Ltd., HackenSack, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/402,091

(22) Filed: Feb. 22, 2012

(65) Prior Publication Data

US 2012/0263772 A1  Oct. 18, 2012

Related U.S. Application Data

(63) Continuation of application No. 12/947,906, filed on Nov. 17, 2010, now Pat. No. 8,124,116, which is a continuation of application No. 11/228,566, filed on Sep. 15, 2005, now Pat. No. 7,879,348.

(51) Int. Cl.
*A61K 51/00* (2006.01)
*A61K 31/655* (2006.01)
*A01N 25/08* (2006.01)
*A01N 37/34* (2006.01)
*A61K 31/275* (2006.01)

(52) U.S. Cl.
USPC ........... 424/409; 119/650; 119/651; 119/652; 514/100; 514/521

(58) Field of Classification Search
None
See application file for complete search history.

(56) References Cited

U.S. PATENT DOCUMENTS

| 4,965,287 | A | 10/1990 | Stendel et al. |
| 5,814,113 | A * | 9/1998 | Neuland ......................... 51/298 |
| 6,620,025 | B2 | 9/2003 | Scheuneman et al. |

(Continued)

FOREIGN PATENT DOCUMENTS

| DE | 202 09 062 U1 | 12/2002 |
| EP | 0 144 721 | 6/1985 |

(Continued)

OTHER PUBLICATIONS (1 page abstract XP-002474403) Basco, B. et al.; "Synergistic prepm. Against parasites of bees" Derwent Publications Ltd., HU 41 594 (1987).

(Continued)

*Primary Examiner* — Ernst Arnold
(74) *Attorney, Agent, or Firm* — Merchant & Gould P.C.

(57) ABSTRACT

Pesticide strips used to control parasitic mites in honeybees. The pesticide strips are designed to have a lifetime or period of existence, after which the strip no longer exists in its original form. The strip breaks down, such as by disintegration, dissolving, decomposition, being eaten or carrier away, or otherwise degrading over time, so that at the end of the recommended lifetime, the strip is no longer in its original form. In most embodiments, at least 50% of the strip is no longer present, and in other embodiments at least 75% of the strip is no longer present. Preferably, at the end of the recommended lifetime, the strip no longer exists, at least the body of the strip that included the active ingredient. With this design, the strip does not provide extended low-dose pesticide that can be detrimental in treating the mites.

10 Claims, 1 Drawing Sheet

U.S. PATENT DOCUMENTS

| | | |
|---|---|---|
| 6,646,014 B2 | 11/2003 | Watkins |
| 6,843,985 B2 | 1/2005 | Erickson, Jr. |
| 7,879,348 B2 | 2/2011 | Volby |
| 8,124,116 B2 | 2/2012 | Volby |
| 2005/0090560 A1 | 4/2005 | Erickson, Jr. et al. |

FOREIGN PATENT DOCUMENTS

| | | |
|---|---|---|
| EP | 0 224 697 A1 | 6/1987 |
| GB | 901693 | 7/1962 |
| HU | 41594 | 5/1987 |
| SU | 1676554 | 9/1991 |

OTHER PUBLICATIONS

XP-002474399) "Fluvalinate—use it right or lose it!," *APIS*, vol. 13, No. 2, http://apis.ifas.ufl.edu/apis95/apfeb95.htm, 4 pages. (Feb. 1995).

(1 page abstract XP-002474400) Sledzinski, B. et al., "Third generation Polish varroacide preparations for honeybee protection," *Pestycydy*, vol. 4, pp. 9-15 (1994).

(2 page abstract XP-002474401) Skinner, J. et al., "Evaluation of honey bee miticides, including temporal and thermal effects on formic acid gel vapors, in the central south-eastern USA," *Journal of Apicultural Research*, vol. 40, Nos. 3-4, pp. 81-89 (2001).

(1 page abstract XP-002474402) Derwent Publications Ltd., "Procedure for combating Varroa ticks in bees—involves placing strips coated with petroleum jelly and dill or fennel oil in bottom of hive," SU 1 676 554 A1, (1991).

Varroa & Small Hive Beetle Control, Mann Lake Ltd. Catalog, pp. 37, 38, 41.

Keeping Healthy Bees, www.mannlakeltd.com/learning/healthy.htm, pp. 1-3, Printed May 9, 2005.

Varroa Mites Infesting Honey Bee Colonies, University of Kentucky Entomology, pp. 1-2, dated Oct. 2001, Printed May 9, 2005.

Search Report and Written Opinion mailed Apr. 10, 2008.

Dow Chemical Information Regarding "Poly-ox" (1995-2010); pre-dates priority date; published prior art information concerning Poly-ox.

EPO comments on related EP Patent dated Oct. 31, 2008.

Varroa & Small Hive Beetle Control, Mann Lake Ltd. Catalog, pp. 37, 38, 41 (pre-dates priority date); available prior to priority date, Sep. 2005.

\* cited by examiner

PESTICIDE STRIPS FOR CONTROL OF MITES IN HONEYBEES

CROSS-REFERENCE TO RELATED APPLICATIONS

This application is a continuing application of U.S. Ser. No. 12/947,906, filed Nov. 17, 2010, which has now issued as U.S. Pat. No. 8,124,116. U.S. Ser. No. 12/947,906 is a continuing application of U.S. Ser. No. 11/228,566 filed Sep. 15, 2005, which issued as U.S. Pat. No. 7,879,348, The complete disclosures of U.S. Ser. Nos. 12/947,906 and 11/228,566 are incorporated herein by reference. A claim of priority to each of U.S. Ser. Nos. 12/947,906 and 11/228,566 is made to the extent appropriate.

FIELD

The present disclosure relates to compositions for use to control parasitic mites in honeybee hives, and use of those compositions. Particularly, this disclosure is directed to pesticide strips used in hives.

BACKGROUND

*Varroa* mites are external honeybee parasites that attack honeybees and can wipe out a colony.

The mites suck the blood from both the adults and the developing brood, weakening and shortening the life span of the ones on which they feed. Emerging brood may be deformed with missing legs or wings. Untreated infestations of *varroa* mites that are allowed to increase will kill honeybee colonies.

Various treatments and pesticides are known for treatment of mites. Fluvalinate, a synthetic pyrenthoroid, available under the designation Apistan™, is a common pesticide for *varroa* mites.

Apistan is available impregnated into plastic strips, which are hung between frames in the hive. CheckMite+™ is another pesticide-impregnated plastic strip that is commonly used. Recommended treatment of mites is to hang two strips (either Apistan, CheckMite+, or other) in the brood nest area of the colony for the allotted time, which is approximately 4 weeks for Apistan and approximately 42-45 days for CheckMite+. After the suggested treatment period, the recommended action is to remove the strips from the hive, as the amount of active ingredient remaining in the strips is typically too low to affect the mites. However, many beekeepers leave the strips in after their useful life.

Leaving the strips in past their useful life can be detrimental to the fight against the mites. Having a low-dose strip in the hive provides a false sense of security to the beekeeper that the hive is being treated. Additionally, extended exposure to low levels of pesticide may build the mites' resistance to the pesticide. Improvements in pesticide strips, and their use, are desired.

SUMMARY OF THE DISCLOSURE

The present disclosure is directed to products used to control parasitic mites in honeybee hives, particularly, pesticide strips used in beehives. The pesticide strips of the present disclosure are designed to have a lifetime or period of existence, after which the strip no longer exists in its original form. The strip is designed to disintegrate, dissolve, be eaten, or otherwise degrade over time, so that at the end of the recommended lifetime, the strip is no longer in its original form. In most embodiments, at least 50% of the strip is no longer present, and in other embodiments at least 75% of the strip is no longer present. Preferably, at the end of the recommended lifetime, the strip no longer exists, at least the body of the strip that included the active ingredient. With this design, the strip does not provide extended low-dose pesticide that can be detrimental in treating the mites.

In one particular aspect of this disclosure, a pesticide strip is provided that has a body comprising a carrier and an active ingredient, the carrier being at least one of gelatin, sugar, starch, or biodegradeable polymer. The active ingredient can be dispersed throughout the carrier or present on a surface.

In another particular aspect, the disclosure is directed to a method of providing an active ingredient to honeybees. The method includes providing a strip in a first form, the strip comprising a carrier and an active ingredient, placing the in a beehive, and then waiting a prescribed time duration, after which time duration the body of the strip is in a second form different than the first form. This second form may be no more than 50% of the first form, or even no more than 25% of the first form. Preferably, the strip no longer exits. The prescribed time duration could be 28 days or 45 days.

Yet another particular aspect of this disclosure is a method of administering an active ingredient to honeybees. The method includes placing a strip in a beehive, the strip comprising a carrier and an active ingredient, releasing the active ingredient from the carrier into the beehive, and having the strip break down. This break down can be at least 50% or even at least 75%. Preferably, the strip breaks down completely and no longer exits.

Additional details regarding active strips according to the present disclosure and methods of using the strips are provided below.

DETAILED DESCRIPTION OF THE DISCLOSURE

Various chemicals are known for treating *varroa* mites, chemicals such as fluvalinate, a synthetic pyrethroid (present in the Apistan product), and organophosphate coumaphos (present in the CheckMite+product). Other chemicals known for the treatment of mites include 2-heptanone, 1-heptanol, ethyl butyrate, benzaldehyde, heptaldehyde, and d-limonene. Formic acid is also used (such as in the product Apicure™). Various "natural" chemicals or formulations are also known for treating *varroa* mites; these are broadly referred to as essential oils. Essential oils that taught to control mites, either by contact with the oil or impairing reproduction, include wintergreen, patchouli oil, tea tree oil, menthol, geranioil, thymol, citral, limoneme, myrcene, and others. See, for example, U.S. Pat. No. 6,646,014 for lists of various suitable essential oils. Generally, these materials are in liquid form.

Figure 1:
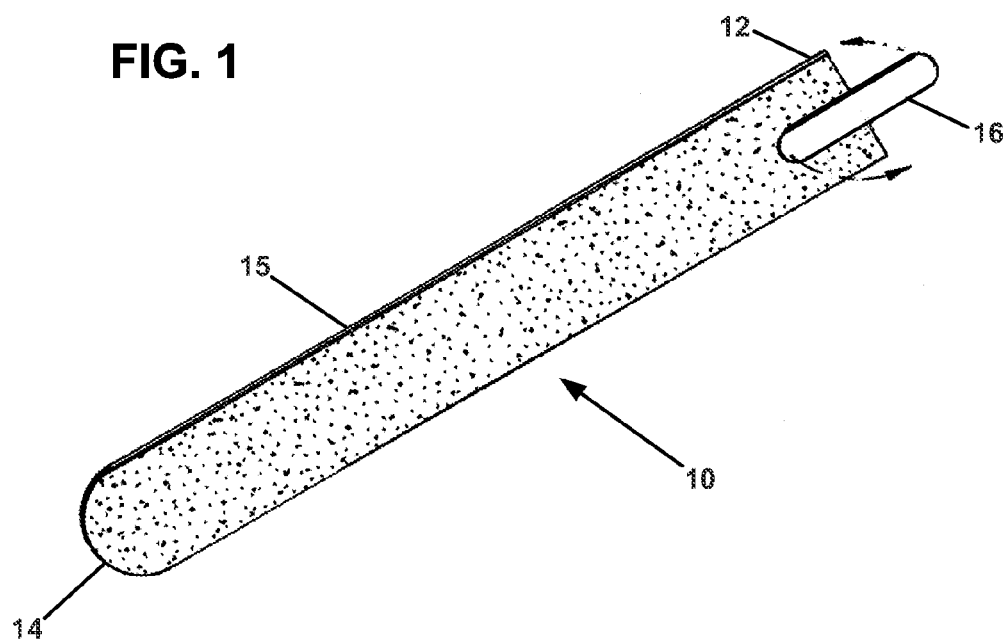
FIG. 1 is a perspective view of a pesticide strip according to the present invention.

In accordance with the present invention, the active ingredient, or pesticide, is carried by a solid strip or device, such as illustrated in FIG. 1. In FIG. 1, strip 10 is shown having a first end 12, an opposite second end 14, and a body 15, which includes the active ingredient either on the surface of body 15 or present through at least a portion of body 15. The active ingredient is preferably one that is used to treat *varroa* mites, however, this technology could be used for other pesticides or medicaments for honeybees, or even for other applications where the introduction of an active ingredient is desired.

Returning to FIG. 1, typically, strip 10 is shaped and sized to depend vertically between frames in the hive. A typically size for strip 10 is about 8 inches long (from first end 12 to second end 14), about 1 inch wide, and about 0.125 inch thick, although strips 10 having a length of 6 to 12 inches, and/or a width of 0.25 inch to 2 inches are often used. It is understood the other sizes of strips would also be suitable. Generally, the strips are fairly thin, being no more than 0.5 inch. Although the typical and preferred form for the pesticide item is a strip, in some embodiments it may be desired to have other shapes, such as more planar (such as sheets), or more monolithic (such as blocks).

Figure 2:
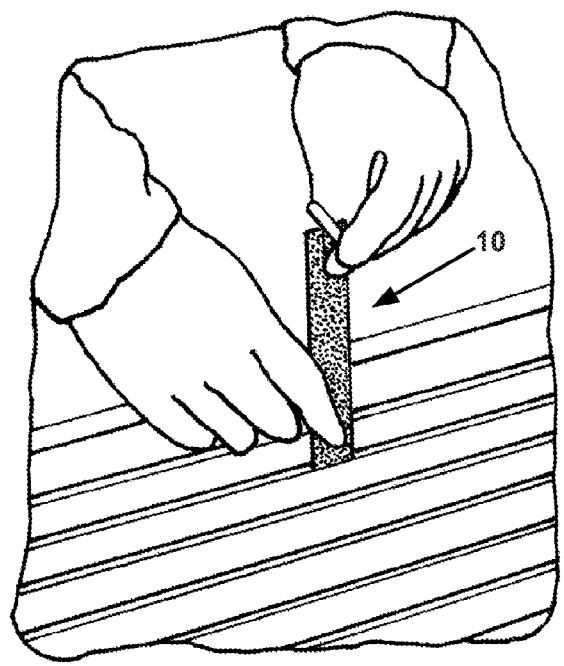
FIG. 2 is a perspective view of a pesticide strip according to the present invention being inserted between frames in a hive.

Strip 10 is illustrated with a hanger mechanism 16 that is configured to retain strip 10 vertically between frames. Hanger mechanism 16 illustrated is pivotal from being planar with body 15 to being perpendicular to body 15, to allow hanging of strip 10. FIG. 2 illustrates strip 10 being inserted between frames in a hive box. Typically, one strip is hung every five frames, although higher and lower densities may be used. It is understood that other configurations for strips are within the scope of this invention. For example, strips according to the invention could be configured for horizontal positioning between adjacent boxes.

The pesticide strips of the present invention are designed to disintegrate, dissolve, decompose, be eaten by bees, disassembled by bees, or otherwise degrade over time, so that at the end of the recommended lifetime the strip is no longer in its original form. By use of the term "break down", "breaks down", or variations herein, what is intended is to cover all methods of the strip changing form, either by disintegrating, dissolving, decomposing, being eaten by bees, being disassembled by bees, or otherwise degrading. Typically, the strip, at the end of the recommended lifetime, the strip has broken down and is less than 50% of its original form, and preferably is less than 25% of its original form. In preferred embodiments, the strip, at least the portion of body 15 having the active ingredient therein or thereon, ceases to exist. That is, 100% of the original strip body no longer exists; or in other words, 0% of the body of the strip remains. It is understood that various portions of strip 10, such as hanger mechanism 16, may remain after the recommended lifetime, although this would be undesired, as such remaining pieces would clutter the hive.

Body 15 of strip 10 has the active ingredient present on or in a carrier, which is typically an inert carrier. The carrier used is selected based on the mode of strip-disappearance desired, but is generally a polymeric or starch or sugar based material. Beeswax is also an acceptable carrier. Various specific examples are provided below.

Generally, to make strip 10 according to the present invention, the active ingredient is dispersed throughout or dissolved in the substantially inert carrier or carrier matrix. The carrier matrix is then molded or otherwise shaped into the desired form, such as strip 10. Molding may be done, for example, by casting or by extrusion. Alternately, the active ingredient is applied, for example by immersion or spraying, to the carrier already formed into the desired shape and size. It is from the carrier that the active ingredient is gradually released in the environment.

Non-limiting examples of suitable carriers that can be used include various gels, waxes (including paraffin wax and beeswax), gelatins, starches (for example, corn based) natural resins, rubbers, elastomers, synthetic and natural polymers, and the like. The carrier is preferably sufficiently strong and rigid to maintain the shape of strip 10 during installation in a beehive.

In one embodiment, the active ingredient is generally released from strip 10 in a controlled manner. The active ingredient may be present throughout or on the carrier matrix itself, which provides controlled release of the active ingredient, typically by diffusion. Additives may be included in the carrier matrix; additives that provide controlled release of the active ingredient. Examples of adjuvant materials that provide controlled release of an active ingredient include porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. At the end of the release of the active ingredient, the body of strip 10, composed of the carrier, disintegrates, dissolves, decomposes, is eaten by bees, disassembled by bees, or otherwise degrades.

It is foreseen, but currently not preferred, that a transport limiting or diffusion limiting layer, such as a membrane, could be provided over the surface of the carrier and the active ingredient to help control the flux of the active ingredient. Various types of transport or diffusion limiting membranes are known.

In another embodiment, the release of the active ingredient occurs as the active ingredient is exposed, due to the carrier breaking down, either by disintegrating, dissolving, decomposing, being eaten or disassembled by bees, or otherwise degrading. That is, new active ingredient is exposed, and optionally released, as the body of strip 10 breaks down and disappears. It is desired that no matter how released, that the active ingredient is at a constant level. It is understood that various factors will affect the rate of active ingredient dispersal and strip disappearance, such as carrier material, density of carrier, concentration of active ingredient, desirability of carrier or strip (for strips that are eaten by the bees), humidity and/or temperature of environment, and the like. Preferably, each of these is taken into consideration in designing strip 10.

Some carrier materials degrade or biodegrade, such as upon exposure to moisture, leaving little or no residue behind. Other carrier materials, such as sugar-based matrices, are eaten by the bees, leaving behind little or no residue. Yet other carrier materials, such as wax, are disassembled by the bees and moved to a different location. Beeswax may be disassembled and used as material for comb, whereas paraffin wax may be carried out of the hive. A combination of the degradation techniques (e.g., dissolving, chewing, eating, etc.) may occur.

Strip 10 of the present invention may be composed of one or more materials, in order to provide a strip that dissolves or degrades, is eaten, or a combination. For example, strip 10 may be made from a combination of sugar and gelatin; the bees would eat the sugar portion of strip 10, and their saliva would dissolve the gelatin portion. The strips may be colored, scented, flavored, or otherwise designed to be more appealing to the bees.

No matter whether dissolved, degraded, decomposed, eaten, carried away, or otherwise destroyed, body 15 of strip 10 breaks down and ceases to exist at the end of the desired life time, usually 28 days or 45-60 days, depending on the active ingredient used and the dosage. Preferably, at least a portion of the strip remains for at least 21 days, which is an effective period for the insecticide to be delivered to the mites; additionally, it is preferred there is no degradation of strip 10 until it is placed in the hive, in contact with the bees. By having the strip no longer exist at the end of the desired lifetime, the opportunity to have low levels of active ingredient remain is eliminated. Additionally, destruction of the strip eliminates the need to remove used strips.

The following specific examples were prepared and tested:

Example 1

Coumaphos Insecticide was Compounded with "Poly-Ox" Water Soluble Resin from Dow Chemical Co. to Form a Mixture Having 10% Active Ingredient Example 2

Fluvalinate Insecticide was Compounded with a Sugar Gel to Form a Mixture Having 10% Active Ingredient The compounds were manually blended with a stir stick while heated so that the active ingredient (i.e., the insecticide) was thoroughly mixed throughout the carrier. While warm, the compounds were cast in a mold to provide a strip approximately 5 inches long by 2 ½ inches wide with a thickness of about 0.25 inch. After cooling, the resulting strips were sufficiently rigid to handle.

The strips were placed in a hive with honeybees for a total of 45 days. Weekly, the strips were visually examined for the extent of degradation, and were weighed. Additionally, the inside of the hive and the area immediately surrounding the hive was visually examined for the presence of dead mites.

The loss of material from the strips was weekly evident. After 45 days, both experimental strips no longer existed; that is, the strips had completely disappeared. It is believed that the strips degraded due to a combination of environmental conditions (e.g., the high level of humidity in the hive) and the mechanical chewing of the strips by the honeybees.

A second set of the same example strips was placed in an air conditioned room, not exposed to honeybees, and was basically left undisturbed. After three months, the strips were intact, even having gained a small amount of mass, it is believed due to moisture absorption.

The inventive pesticide has been described with reference to various specific and preferred embodiments and techniques, and in specific working examples. However, it should be understood that many variations and modifications could be made from the specific disclosure above. For example, although the illustrated strips are designed to depend between frames, other orientations are within the scope of this disclosure, as are other shapes and sizes. As another example, it is within the scope of the disclosure to have other shaped items with active ingredients, not just strips, which dissolve, degrade, or get eaten by bees or other insects or animals. Other variations are within the spirit and scope of this disclosure.

What is claimed:

1. A pesticide strip for positioning in a bee hive, for mite control; the strips comprising:
   (a) moisture degradable carrier matrix comprising poly (ethylene oxide) and,
   (b) active ingredient comprising pesticide for mites;
   (c) the carrier matrix being completely degradable in the hive and being sized to have a portion present in the hive, in use, for at least 21 days and to thereafter further degrade, the degradation being at a rate such that no more than 25% of the original carrier matrix is present after a selected time period from within the range of 45-60days.

2. The pesticide strip according to claim 1 wherein:
   the strip has a thickness of no more than 0.5 mm, a length within the range of 6 to 12 inches; and, a width within the range of 0.25-2inches.

3. The pesticide strip according to claim 1 further comprising:
   porous particulate in the carrier matrix.

4. The pesticide strip according to claim 3 wherein:
   the porous particulate comprises particulate selected from the group consisting essentially of: silica, perlite, talc, and clay.

5. A pesticide strip according to claim 3 wherein:
   the porous particulate comprises clay.

6. A method of providing an active ingredient to honeybees for mite control; the method comprising the steps of
   (a) providing a strip comprising:
      (i) moisture degradable carrier matrix comprising poly (ethylene oxide); and,
      (ii) active ingredient comprising pesticide for mites;
   positioning the strip in an occupied bee hive;
   (b) (i) the carrier matrix being formulated to be completely degradable in the hive and so as to have a portion of the carrier matrix remaining when positioned in the hive for at least 21 days and the degradation being at a rate such that no more than 25% of the original carrier matrix is present after a selected time period from within the range of 45-60 days;
   (c) ( leaving the strip in the hive at a location where it can be contacted by bees, for a period of at least 21 days.

7. The method according to claim 6 wherein:
   the strip has a thickness of no more than 0.5 inch; a length within the range of 6 to 12 inches; and, a width within the range of 0.25-2 inches.

8. The method according to claim 7 wherein:
   the step of providing a strip includes providing porous particulate in the carrier matrix.

9. The method according to claim 7 wherein;
   the step of providing a strip comprises using, as the porous particulate, particulate selected form the group consisting essentially of: silica, perlite, talc, and clay.

10. The method according to claim 7 wherein:
    the porous particulate in the carrier matrix is clay.

* * * * *